United States Patent [19]

Thalen

[11] 4,030,508
[45] June 21, 1977

[54] LOW OUTPUT ELECTRODE FOR CARDIAC PACING

[75] Inventor: Hilbert J. Th. Thalen, Duinkampen, Netherlands

[73] Assignee: Vitatron Medical B.V., Dieren, Netherlands

[22] Filed: Feb. 4, 1976

[21] Appl. No.: 655,156

[52] U.S. Cl. .............................. 128/418; 128/419 P
[51] Int. Cl.² ...................... A61N 1/04; A61N 1/36
[58] Field of Search ................ 128/404, 418, 419 P

[56] References Cited

UNITED STATES PATENTS

| | | | |
|---|---|---|---|
| 3,568,660 | 3/1971 | Crites | 128/419 P X |
| 3,683,932 | 8/1972 | Cole | 128/419 P |
| 3,731,376 | 5/1973 | Ackerman | 128/418 X |
| 3,749,101 | 7/1973 | Williamson | 128/418 |
| 3,814,104 | 6/1974 | Imich | 128/418 |
| 3,902,501 | 9/1975 | Citron | 128/404 |
| 3,941,135 | 3/1976 | Sturm | 128/404 X |
| 3,977,411 | 8/1976 | Hughes, Jr. | 128/404 X |

FOREIGN PATENTS OR APPLICATIONS 2,347,720  4/1974  Germany ......................... 128/418

OTHER PUBLICATIONS

"USCI–Cardio. Electrodes, Pacing . . . Catheters," June 1974.
Hopps et al., "Electrical Treatment . . . Arrest," Surgery, vol. 36, No. 4, Oct. 1954, pp. 833–849.

*Primary Examiner*—Robert W. Michell
*Assistant Examiner*—Lee S. Cohen
*Attorney, Agent, or Firm*—Woodcock, Washburn, Kurtz & Mackiewicz

[57] ABSTRACT

An electrode for use in combination with a cardiac pacer for endocardial stimulation, having an electrode contact tip at the distal end which has an annular shape with rounded edges for providing a very small stimulating surface, with the largest possible area of such surface in optimal position for direct contact with the heart muscle.

8 Claims, 4 Drawing Figures

LOW OUTPUT ELECTRODE FOR CARDIAC PACING

BACKGROUND OF THE INVENTION

1. Field of the Invention

This invention relates to electrodes, or catheters, and, more particularly, to unipolar electrodes adapted for use in combination with cardiac pacers for low power drain stimulation of a patient's heart.

2. Description of the Prior Art

In the approximately 14 years that implantable cardiac pacing devices have been available, a great number of important technological develpments have taken place which have greatly increased the efficiency, reliability and lifetime of implantable pacers. The pacing devices themselves, comprising the battery power source and the electronic circuitry, have over this period of time incorporated substantial changes. In addition, the electrodes, or cathaters by which the pacer produced stimulus pulses are delivered to the heart tissue, have also experienced significant design changes. Throughout the history of development of cardiac pacing systems, a foremost objective has been to utilize the available power in the implanted device to the maximum possible extent. In order to do this, it has become recognized that the system, comprised of both the pacer device and the electrode, must be optimally matched in order to most efficiently deliver the stimulus pulses.

Another area of great concern where improvement is still sought is in the area of providing and maintaining good electrode contact at the heart, so as to ensure good stimulus threshold. The electrode design must be such that the stimulus pulses are delivered effectively to the heart tissue. This requirement generally suggests that the distal tip of the electrode must be sufficiently well positioned so that the best possible threshold is obtained. However, positioning can be a difficult procedure, and the physician would prefer that the positioning not be so critical. An alternate approach is to make the electrode contact surface large enough so that the position of the electrode tip is not critical. This possibility is not a feasible one, since a large surface electrode would present a very low output resistance to the pacer, and cause substantial and unnecessary current drain. Further, the large surface would result in the current density of the delivered stimulus pulse being very low, and the lower the current density the less chance of cardiac stimulation. For a unipolar electrode system, the electrical field emanates from the single contact surface and passes through the ventricular wall to the distant indifferent electrode. It is well understood that the larger the surface of the contact element, the more dispersed is the emanating electrical field, and consequently the smaller the ability of a pulse of a given power to produce cardiac stimulation.

To overcome these difficulties, a wide variety of electrode designs have been developed and utilized. The predominant design philosophy currently is to reduce the contact surface, so as to increase current intensity and to achieve reliable stimulation with lower output. However, mere reduction of the electrode surface carries with it the adverse feature that positioning may be more critical. To overcome this, some electrode designs have incorporated features whereby the distal tip actually penetrates into the endocardium, as for example using a type of corkscrew. However, this general arrangement isn't satisfactory in that it results in muscle damage and tissue build-up which is detrimental to long term optimization of stimulus thereshold. Further, even where the distal tip of the electrode is held firmly in contact with the endocardium, it remains a question whether the available contact surface is properly positioned relative to the endocardium. For example, a typical contact tip as found in the prior art has the form of a cylinder with a closed distal end, and for this shape the stimulus current delivery is inefficient depending upon whether the heart tissue at the point of contact is relatively flat, convex or concave, and how the tip interfaces with the heart tissue. Frequently in placement of an electrode with such a tip, only a corner between the end and the side cylindrical wall will be actually positioned in contact with the heart tissue, which can result in a high stimulus threshold. It is thus seen that the solution to the problem requires not simply making the electrode small, but both shaping and positioning it at the distal end of the electrode so that positioning is relatively non-critical.

SUMMARY OF THE INVENTION

It is a prime object of this invention to provide an electrode for cardiac pacing having a distal tip of low conductive surface area for permanent endocardial stimulation, to be used in combination with a cardiac pacer producing output pulses with a relatively low energy content.

It is a further object of this invention to provide an electrode for use in a cardiac pacer system, the electrode having an annular shape designated to ensure that the largest possible area of a very small stimulating surface of such electrode tip is likely to be in direct contact with the heart muscle, so as to provide a low stimulation threshold.

It is a further object of this invention to provide a low output electrode for use in combination with a cardiac pacer producing relatively low energy stimulus pulses, the low output electrode having an annular shape positioned on the distal tip of the electrode so as to maximize the electric field intensity in the heart tissue when each stimulus pulse is delivered.

In accordance with the above objects, there is provided a pacing electrode having at its far distal tip an annularly shaped contact surface for delivering stimulus pulses, the surface being generally concentric with respect to the axis of the electrode tip, the surface having a generally circular opening at the center thereof which is occupied by a nonconductive material, the surface also having rounded edges. The rounded annular shape of the contact surface permits a very small stimulating surface, while optimally interfacing with the heart endocardium to enable positioning of the largest possible area in direct contact with the endocardium and to provide high field intensity conduction of stimulus pulses.

DESCRIPTION OF THE PREFERRED EMBODIMENT

Figure 1:
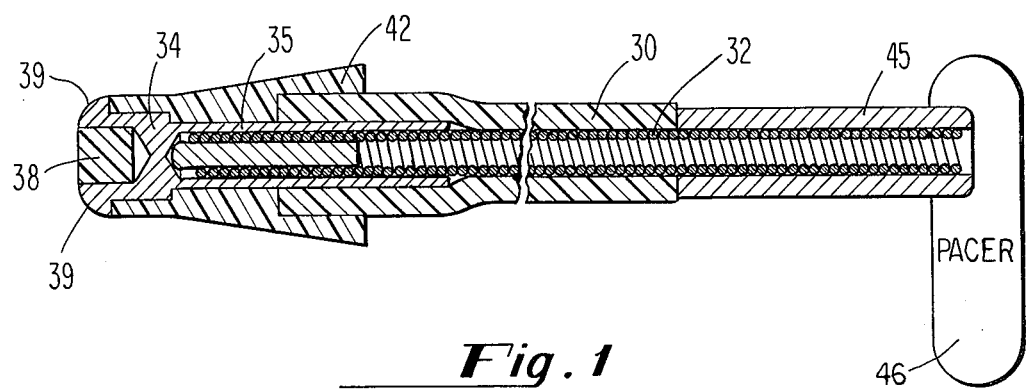
FIG. 1 is a cross sectional view illustrating in detail the construction of the electrode of this invention.

Referring now to FIG. 1, there is shown an electrode having an outer casing 30 made suitably of silicone rubber or any like material, the electrode being of a conventional tubular form and adapted for insertion into a patient's cardiac system. FIG. 1 is shown with the proximal and distal ends broken, but it is to be understood that the length of the electrode may be any length desired. The electrode diameter is typically 2.5 mm. Running substantially the length of the electrode is a helical conduction lead 32, which is suitably constructed of Elgiloy (Registered Trademark) wire, having a typical diameter of 0.25 mm, and encased within casing 30. The helical construction is preferred so as to permit use of a stilette, or a mandrin with the electrode. At the distal end of the electrode, as seen at the left of FIG. 1, a conducting element 34 suitably made of platinum iridium is positioned in good electrical contact with the end of conductor 32. Portion 35 as shown in FIG. 1 envelops conductor 32, providing the good electrical contact. Conductive tip portion 39 extends axially to the far distal tip, where it is brought to the surface with an annular form. The exposed surface portion 39 is comprised of rounded edges which form a rounded ring or annular section at the far distal tip. An element made of an isolating material 38, suitably silicone rubber, is positioned within the annular ring 39.

In practice, the outer diameter of the electroe ring tip 30 is about 2.7 mm, and the axial length of the tip is about 0.7 mm. The element 38 is at least 1.0 mm in diameter and preferably about 1.3 mm in diameter, such that the stimulating surface is only about 8 mm². The electrode tip is completed by a silicone rubber flange 42, which is designed to help prevent displacement of the electrode in the initial days following implantation. As seen also in the illustration of FIG. 4, the tip of the electrode provides a curved, or rounded annular surface, which has the advantage of not having any sharp edges which could cause perforation or damage during insertion. More importantly, the surface area of the electrode is reduced at least by the space taken up by center nonconductive portion 38. It can be seen that if the electrode is positioned precisely normally to the heart tissue, whether such tissue be flat, convex or concave, the annular portion 39 will provide an effective electric field. If the electrode tip is positioned at any angle relative to the heart tissue with which it comes into contact, the rounded edge will still provide a good direct surface contact. Thus, the shape of the surface is optimally designed to provide the best direct contact with the smallest total surface.

Figure 4:
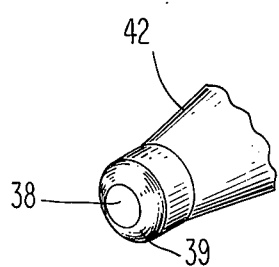
FIG. 4 is an end perspective view of the contact tip of the electrode of this invention.

In the prior art, electrodes are shown having tips positioned at the very distal end thereof, where such tips are cylindrical but also solid. In other words, the tip has an exposed surface at the side walls of the cylinder which are parallel with the electrode casing, but also has a solid uniform surface at the end of the tip, the end being the portion substantially normal to the electrode axis. Because of the solid end, such prior art contact surfaces are not annular. Annular as used here means that the portion of the surface which closes the contact tip at the tip end thereof has a central opening, such that when viewed axially from a point proximal to the very end of the electrode the contact surface appears ring-like in shape. As shown in FIGS. 1 and 4, the central opening in the contact portion of the tip defines a plane substantially normal to the electrode axis, and as used in the claims annular means having such a space, or opening. It is also to be noted that the curve 39 of the annular contact surface extends from the electrode wall which is parallel to the axis, to the plane normal to the axis and at the extreme distal end of the electrode. This is referred to as a 90° curve, or 90° rounded edge. As used, the term 90° rounded edge is understood to mean about 90°, and may vary ± from exactly 90°.

Still referring to FIG. 1, the proximal end of the electrode terminates with an extended portion of conductor 32. This portion is illustrated as connected electrically to a terminal element 45 of a pacer 46. Within the scope of this invention, the proximal end may have any suitable design for connection to different pacers or different stimulus generating devices.

Figure 2:
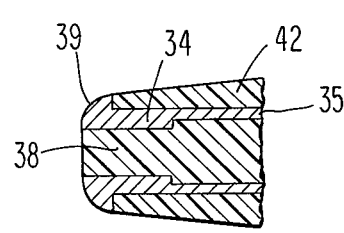
FIG. 2 is a cross sectional view of an alternate form of the electrode tip.

Referring now to FIG. 2, there is illustrated an alternate embodiment of the tip. In this case, the silicone rubber flange 42 is designated to angle radially outward as it extends proximally. In addition, the center nonconducting element 38 is extended axially proximally back to the helical conductor 32. This embodiment illustrates that the internal design of the conducting tip element 34 is not critical to the efficiency of the electrode, and is a design variable.

Figure 3:
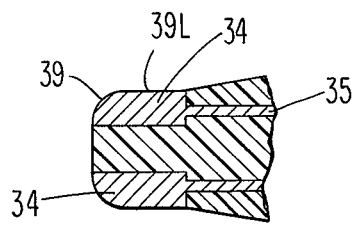
FIG. 3 is a third partial detailed view of another form of the contact tip surface of the electrode of this invention.

Referring to FIG. 3, there is shown an alternate embodiment wherein the outside annular ring 39 of conducting tip 34 extends proximally by a small length designated as 39L. This embodiment may be utilized where it is desired to increase slightly the exposed conductive surface of the electrode tip.

The electrode of this invention has been tested and has been found to possess definite operational advantages. In insertion and positioning of the electrode, it is the same as an ordinary catheter, requiring no special procedures or critical maneuvers. At the same time, due to its small stimulating surface area stimulation threshold is low, resulting in requiring a smaller current drain from the pacer. The combination of a pacer 46 delivering stimulus signals limited to about 0.5 ms pulse duration, and the electrode of this invention with an exposed stimulating tip surface area no greater than about 8 mm², has been found to be uniquely efficient in minimizing the pulse energy required for stimulation and thereby in increasing pacer longevity. Additionally, due to the rounded edge shape of the stimulating tip, there is less risk of damage to the patient's cardiovascular system at time of insertion and implant, such as by vessel perforation from a sharp edge. It has also been found that the electrode of this invention has a small polarization, and the combination of small surface area and small polarization results in an increase in power utilization efficiency as compared to other prior art conventional electrodes.

I claim:
1. A catheter for use in a cardiac pacing system, the catheter serving to deliver stimulus pulses from a pacer to a patient's heart, said catheter comprising:
    a. a conductor extending substantially the length of the catheter, and having an insulating casing around it;
    b. a stimulating tip at one end of said catheter, said tip connected electrically to said conductor and having a rounded annular exposed surface, said exposed surface defining a central opening having a diameter of at least 1 mm and having an axial length much less than its outer diameter; and c. an element of isolating material positioned within said opening.

2. The catheter as described in claim 1, wherein said annular surface consists only of a 90° rounded edge.

3. The catheter as described in claim 1, wherein said annular tip surface is rounded with a 90° edge.

4. The catheter as described in claim 4, comprising a flange made of an insulating material connected to said casing at said one end of said catheter, said flange being adapted to maintain said catheter tip securely in contact with the heart tissue of said patient.

5. The catheter as described in claim 1, wherein said annular surface is limited in area to 8 mm².

6. A cardiac pacing system for delivering stimulus pulses to the heart of a patient, comprising:
   a. pacer means for generating stimulus signals limited in length to about 0.5 ms;
   b. a catheter for delivering stimulus pulses from said pacer means to a patient's heart, said catheter having a conductor extending substantially the length of the catheter and having an insulating casing around said conductor, and connecting means for connecting a first end of said conductor to the output of said pacer means;
   c. said catheter having a stimulating tip connected to said conductor at its opposite said first end, said stimulating tip having an exposed surface which is annular in shape and defines a central opening having a diameter of at least 1.0 mm and which has a surface area limited to 8 square millimeters; and
   d. an element of isolating material positioned in said opening.

7. The cardiac pacing system as described in claim 6, wherein said shape has an axial length much less than said opening diameter.

8. The cardiac pacing system as described in claim 7, wherein said annular shape comprises a 90° rounded edge.

* * * * *

UNITED STATES PATENT AND TRADEMARK OFFICE
CERTIFICATE OF CORRECTION

PATENT NO. : 4,030,508
DATED : June 21, 1977
INVENTOR(S) : Hilbert J. Th. Thalen It is certified that error appears in the above-identified patent and that said Letters Patent are hereby corrected as shown below:

Column 1, line 62, after "lower", insert --power--.

Column 2, line 3, delete "there-" and insert --thre- --.

Column 3, line 30, delete "electroe" and insert --electrode--.

Column 5, line 7, delete "4", second occurrence, and insert therefor --3--.

Column 6, line 6, before "opposite", insert --end--.

Signed and Sealed this

Fifteenth Day of November 1977

[SEAL]

Attest:

RUTH C. MASON
*Attesting Officer*

LUTRELLE F. PARKER
*Acting Commissioner of Patents and Trademarks*